US008447045B1

(12) United States Patent
Laroche (10) Patent No.: US 8,447,045 B1
(45) Date of Patent: May 21, 2013

(54) MULTI-MICROPHONE ACTIVE NOISE CANCELLATION SYSTEM

(75) Inventor: Jean Laroche, Santa Cruz, CA (US)

(73) Assignee: Audience, Inc., Mountain View, CA (US)

( * ) Notice: Subject to any disclaimer, the term of this patent is extended or adjusted under 35 U.S.C. 154(b) by 233 days.

(21) Appl. No.: 12/876,861

(22) Filed: Sep. 7, 2010

(51) Int. Cl.
*A61F 11/06* (2006.01)
*G10K 11/16* (2006.01)

(52) U.S. Cl.
USPC ...... 381/71.1; 381/71.6; 381/71.8; 381/71.11

(58) Field of Classification Search
USPC ............... 381/71.1, 71.6, 71.11, 71.12, 73.1, 381/94.1, 93
See application file for complete search history.

(56) References Cited

U.S. PATENT DOCUMENTS

| 8,160,265 B2 | 4/2012 | Mao et al. | |
| 8,184,822 B2 * | 5/2012 | Carreras et al. | 381/71.6 |
| 8,184,823 B2 * | 5/2012 | Itabashi et al. | 381/74 |
| 2009/0175466 A1 * | 7/2009 | Elko et al. | 381/94.2 |
| 2011/0158419 A1 | 6/2011 | Theverapperuma et al. | |

* cited by examiner

*Primary Examiner* — Vivian Chin
*Assistant Examiner* — Ammar Hamid
(74) *Attorney, Agent, or Firm* — Carr & Ferrell LLP (57) ABSTRACT

The present technology provides systems and methods for robust feedforward active noise cancellation which can overcome or substantially alleviate problems associated with the diverse and dynamic nature of the surrounding acoustic environment. A multi-faceted analysis decouples the background noise within the earpiece from the acoustic wave (e.g. the anti-noise and desired audio) generated by an audio transducer within the earpiece. A difference signal is formed utilizing monitoring signals captured by array of monitoring microphones within the earpiece. The difference signal is formed such that contributions due to the acoustic wave generated by the audio transducer are selectively attenuated. As a result, the difference signal indicates an acoustic energy level of the background noise within the earpiece.

20 Claims, 9 Drawing Sheets

MULTI-MICROPHONE ACTIVE NOISE CANCELLATION SYSTEM

BACKGROUND

1. Field of the Invention

The present invention relates generally to audio processing, and more particularly to techniques for active noise cancellation.

2. Description of Related Art

An active noise cancellation (ANC) system in an earpiece-based audio device can be used to reduce background noise. The ANC system forms a compensation signal adapted to cancel background noise at a listening position inside the earpiece. The compensation signal is provided to an audio transducer (e.g. a loudspeaker) which generates an "anti-noise" acoustic wave. The anti-noise acoustic wave is intended to attenuate or eliminate the background noise at the listening position via destructive interference, so that only the desired audio remains. Consequently, the combination of the anti-noise acoustic wave and the background noise at the listening position results in cancellation of both and hence a reduction in noise.

ANC systems may generally be divided into feedforward ANC systems and feedback ANC systems. In a typical feedforward ANC system, a reference microphone provides a reference signal based on the background noise captured at a reference position. The reference signal is then used by the ANC system to predict the background noise at the listening position so that it can be cancelled. Typically, this prediction utilizes a transfer function which models the acoustic path from the reference position to the listening position. Active noise cancellation is then performed to form a compensation signal adapted to cancel the noise, whereby the reference signal is inverted, weighted and delayed or more generally filtered based on the transfer function.

Errors in feedforward active noise cancellation can occur due to the difficultly in forming a transfer function which accurately models the acoustic path from the reference position to the listening position. Specifically, since the surrounding acoustic environment is rarely fixed, the background noise at the listening position is constantly changing. For example, the location and number of noise sources which form the resultant background noise can change over time. These changes affect the acoustic path from the reference position to the listening position. For example, the propagation delay of the background noise between the reference position and the listening position depends on the direction (or directions) the background noise is coming from. Similarly, the amplitude difference of the background noise at the reference position and at the listening position may be direction dependent.

In a feedforward ANC system, an error microphone may also be placed within the earpiece to provide an error signal. The error signal is intended to indicate the residual noise that remains within the earpiece after cancellation has taken place. The ANC system can then adjust the parameters of the transfer function in an attempt to drive the error signal to zero. However, since the error microphone also captures the desired audio as output by the audio transducer, it can be difficult to accurately determine the residual noise. In addition, it can be difficult to avoid unwanted direct feedback of the desired audio through the reference microphone, which can lead to stability problems for the ANC system.

If the transfer function used to model the acoustic path from the reference position to the listening position is even slightly incorrect, residual noise will remain at the listening position. The residual noise can interfere with the listening experience of the desired sound, and is annoying. In some instances, errors in the transfer function may result in the generation of an anti-noise acoustic wave that constructively interferes with the background noise at the listening position. In such a case, the combination of the anti-noise acoustic wave and the background noise may result in an increase in the noise at the listening position, rather than a decrease.

It is therefore desirable to provide active noise cancellation techniques which can increase the quality and robustness of active noise cancellation systems in diverse acoustic environments.

SUMMARY

The present technology provides systems and methods for robust feedforward active noise cancellation which can overcome or substantially alleviate problems associated with the diverse and dynamic nature of the surrounding acoustic environment. The present technology carries out a multi-faceted analysis to decouple the background noise within the earpiece from the acoustic wave (e.g. the anti-noise and desired audio) generated by an audio transducer within the earpiece. A difference signal is formed utilizing monitoring signals captured by array of monitoring microphones within the earpiece. The difference signal is formed such that contributions due to the acoustic wave generated by the audio transducer are selectively attenuated. As a result, the difference signal indicates an acoustic energy level of the background noise within the earpiece. The difference signal is then utilized to determine characteristics of the acoustic path between a reference position where the noise is captured, and a desired position where the noise is to be cancelled. These characteristics are used to form a feedforward signal adapted to cancel the noise at the desired position to improve sound quality.

A method for reducing an acoustic energy level at a listening position as described herein includes generating a feedforward signal from a primary acoustic wave received at a reference position. A secondary acoustic wave is then generated based on the feedforward signal, the secondary acoustic wave being adapted to reduce the acoustic energy level at the listening position. The primary and secondary acoustic waves are received at a first monitoring position to form a first monitoring signal. The primary and secondary acoustic waves are also received at a second monitoring position to form a second monitoring signal. A feedback signal is then formed based on the first and second monitoring signals, the feedback signal indicating an acoustic energy level of the primary acoustic wave at the listening position. The feedforward signal is then modified based on the feedback signal.

A system for reducing an acoustic energy level at a listening position as described herein includes a reference microphone to receive a primary acoustic wave at a reference position to form a reference signal. A feedforward module generates a feedforward signal based on the reference signal. An audio transducer generates a secondary acoustic wave based on the feedforward signal, the secondary acoustic wave being adapted to reduce the acoustic energy level at the listening position. A first monitoring microphone receives the primary and secondary acoustic waves at a first monitoring position to form a first monitoring signal. A second monitoring microphone receives the primary and secondary acoustic waves at a second monitoring position to form a second monitoring signal. A feedback module then forms a feedback signal based on the first and second monitoring signals, the feedback signal indicating an acoustic energy level of the primary acoustic wave at the listening position. The feedforward module then modifies the feedforward signal based on the feedback signal.

A computer readable storage medium as described herein has embodied thereon a program executable by a processor to perform a method for reducing an acoustic energy level at a listening position as described above.

Other aspects and advantages of the present invention can be seen on review of the drawings, the detailed description, and the claims which follow.

DETAILED DESCRIPTION

The present technology provides systems and methods for robust feedforward active noise cancellation which can overcome or substantially alleviate problems associated with the diverse and dynamic nature of the surrounding acoustic environment. The present technology carries out a multi-faceted analysis to decouple the background noise within the earpiece from the acoustic wave (e.g. the anti-noise and desired audio) generated by an audio transducer within the earpiece. A difference signal is formed utilizing monitoring signals captured by an array of monitoring microphones within the earpiece. The difference signal is formed such that contributions due to the acoustic wave generated by the audio transducer are selectively attenuated. As a result, the difference signal indicates an acoustic energy level of the background noise within the earpiece.

The difference signal is then utilized to determine characteristics of the acoustic path between a reference position where the noise is captured, and a desired position where the noise is to be cancelled. These characteristics are used to form a feedforward signal adapted to cancel the noise at the desired position to improve sound quality. By forming the feedforward signal based on the decoupled background noise within the earpiece, the techniques described herein can accurately model the transfer function from the reference position to the desired position. In doing so, the feedforward active noise cancellation techniques described herein can achieve optimal noise cancellation at the desired location, thereby increasing the quality and robustness of active noise cancellation in diverse acoustic environments.

Embodiments of the present technology may be practiced on any earpiece-based audio device that is configured to receive and/or provide audio such as, but not limited to, cellular phones, MP3 players, phone handsets and headsets. While some embodiments of the present technology will be described in reference to operation on a cellular phone, the present technology may be practiced on any audio device.

Figure 1:
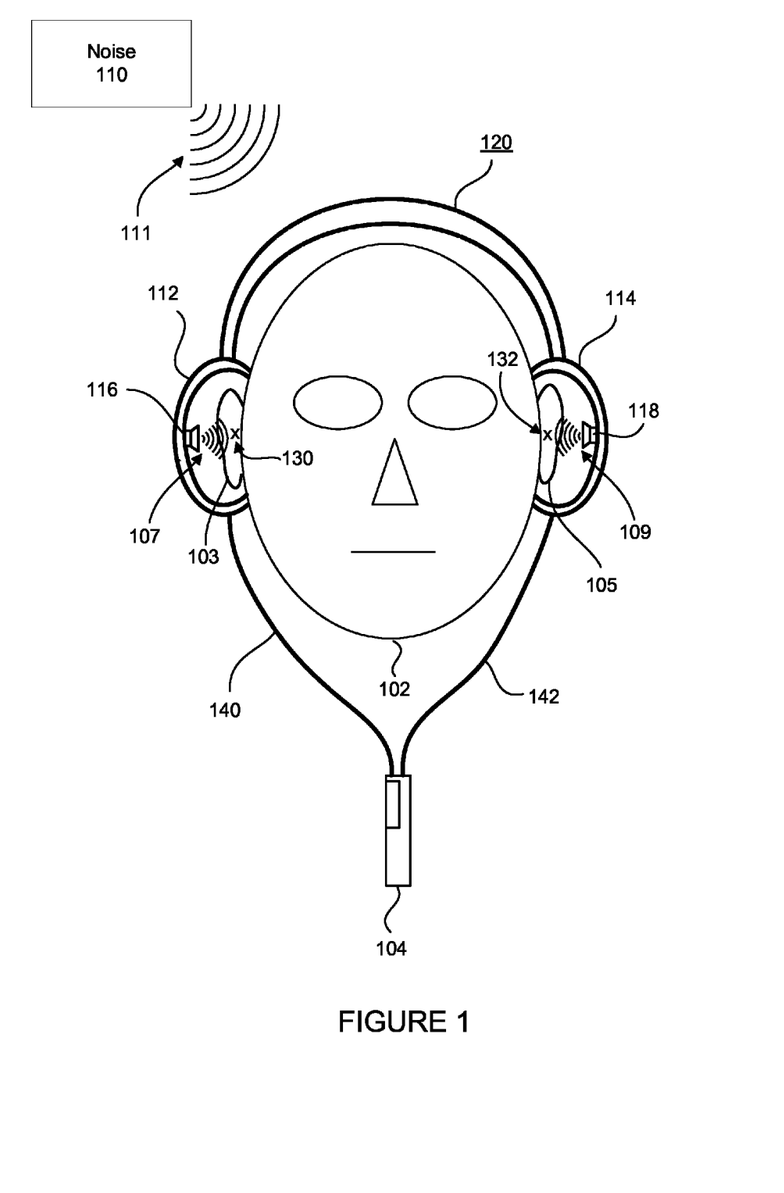
FIG. 1 is an illustration of an environment in which embodiments of the present technology may be used.

FIG. 1 is an illustration of an environment in which embodiments of the present technology may be used. An audio device 104 may act as a source of audio content to a headset 120 which can be worn over or in the ears 103, 105 of a user 102. The audio content provided by the audio device 104 may for example be stored on a storage media such as a memory device, an integrated circuit, a CD, a DVD, etc for playback to the user 102. The audio content provided by the audio device 104 may include a far-end acoustic signal received over a communications network, such as speech of a remote person talking into a second audio device. The audio device 104 may provide the audio content as mono or stereo acoustic signals to the headset 120 via one or more audio outputs. As used herein, the term "acoustic signal" refers to a signal derived from or based on an acoustic wave corresponding to actual sounds, including acoustically derived electrical signals which represent an acoustic wave.

In the illustrated embodiment, the exemplary headset 120 includes a first earpiece 112 positionable on or in the ear 103 of the user 102, and a second earpiece 114 positionable on or in the ear 105 of the user 102. Alternatively, the headset 120 may include a single earpiece. The term "earpiece" as used herein refers to any sound delivery device positionable on or in a person's ear.

The audio device 104 may be coupled to the headset 120 via one or more wires, a wireless link, or any other mechanism for communication of information. In the illustrated embodiment, the audio device 104 is coupled to the first earpiece 112 via wire 140, and is coupled to the second earpiece 114 via wire 142.

The first earpiece 112 includes an audio transducer 116 which generates an acoustic wave 107 proximate the ear 103 of the user 102 in response to a first acoustic signal. The second earpiece 114 includes an audio transducer 118 which generates an acoustic wave 109 proximate the ear 105 of the user 102 in response to a second acoustic signal. Each of the audio transducers 116, 118 may for example be a loudspeaker, or any other type of audio transducer which generates an acoustic wave in response to an electrical signal.

As described below, the first acoustic signal includes a desired signal such as the audio content provided by the audio device 104. The first acoustic signal also includes a first feedforward signal adapted to cancel undesired background noise at a first listening position 130 using the techniques described herein. Similarly, the second acoustic signal includes a desired signal such as the audio content provided by the audio device 104. The second acoustic signal also includes a second feedforward signal adapted to cancel undesired background noise at a second listening position 132 using the techniques described herein. In some alternative embodiments, the desired signals may be omitted.

As shown in FIG. 1, an acoustic wave (or waves) 111 will also be generated by noise 110 in the environment surrounding the user 102. Although the noise 110 is shown coming from a single location in FIG. 1, the noise 110 may include any sounds coming from one or more locations that differ from the location of the transducers 116, 118 and may include reverberations and echoes. The noise 110 may be stationary, non-stationary, and/or a combination of both stationary and non-stationary noise.

The total acoustic wave at the first listening position 130 is a superposition of the acoustic wave 107 generated by the transducer 116 and the acoustic wave 111 generated by the noise 110. The first listening position 130 may for example be in front of the eardrum of ear 103, where the user 102 will hear it. As described herein, the portion of the acoustic wave 107 due to the first feedforward signal is configured to destructively interfere with the acoustic wave 111 at the first listening position 130. In other words, the combination of the portion of the acoustic wave 107 due to the first feedforward signal and the acoustic wave 111 due to the noise 110 at the first listening position 130 results in cancellation of both and hence a reduction in the acoustic energy level of noise at the first listening position 130. As a result, the portion of the acoustic wave 107 due to the desired audio signal remains at the first listening position 130, where the user 102 will hear it.

Similarly, the total acoustic wave at the second listening position 132 is a superposition of the acoustic wave 109 generated by the transducer 118 and the acoustic wave 111 generated by the noise 110. The second listening position 132 may for example be in front of the eardrum of the ear 105. Using the techniques described herein, the portion of the acoustic 109 due to the second feedforward signal is configured to destructively interfere with the acoustic wave 111 at the second listening position 132. In other words, the combination of the portion of the acoustic wave 109 due to the second feedforward signal and the acoustic wave 111 due to the noise 110 at the second listening position 132 results in cancellation of both. As a result, the portion of the acoustic wave 109 due to the desired signal remains at the second listening position 132, where the user 102 will hear it.

Figure 2:
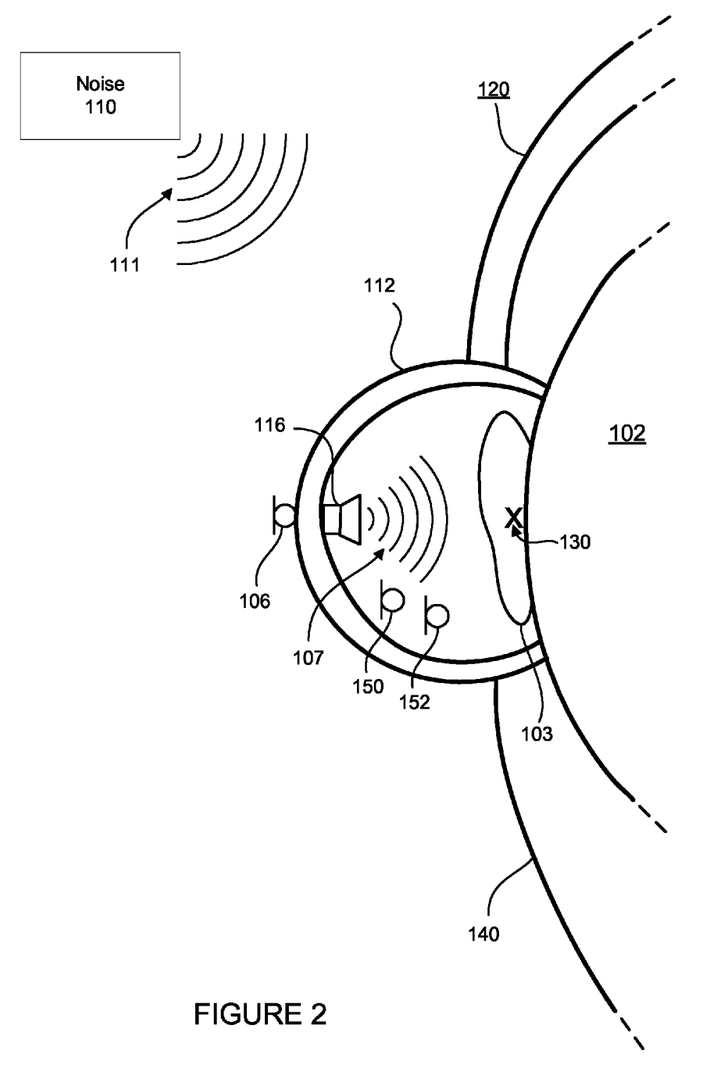
FIG. 2 is an expanded view of FIG. 1.

The first earpiece 112 is representative of the first and second earpieces 112, 114. FIG. 2 is an expanded view of the first earpiece 112. In the following discussion, active noise cancellation techniques are described herein with reference to the first earpiece 112. It will be understood that the techniques described herein can also be extended to the second earpiece 114 to perform active noise cancellation at the second listening position 132.

As shown in FIG. 2, the first earpiece 112 includes a reference microphone 106 at a reference position on the outside of the first earpiece 112. The acoustic wave 111 due to the noise 110 is picked up by the reference microphone 106. The signal received by the reference microphone 106 is referred to herein as the reference signal r(t).

As described below, parameters of a transfer function are then computed to model the acoustic path from the location of the reference microphone 106 to the first listening position 130. The transfer function may incorporate characteristics of the acoustic path, such as one or more of an amplitude, phase shift and time delay from the reference microphone 106 to the first listening position 130. The transfer function can also model the reference microphone 106 response, the transducer 116 response, and the acoustic path from the transducer 116 to the first listening position 130.

The reference signal r(t) is then filtered based on the transfer function to form feedforward signal f(t). An acoustic signal t(t), which includes the feedforward signal f(t) and optionally a desired signal s(t) from the audio device 104, is provided to the audio transducer 116. Active noise cancellation is then performed at the first listening position 130, whereby the audio transducer 116 generates the acoustic wave 107 in response to the acoustic signal t(t).

As shown in FIG. 2, the first earpiece 112 includes a first monitoring microphone 150 at a first monitoring position within the first earpiece 112. The first earpiece 112 also includes a second monitoring microphone 152 at a second monitoring position.

The total acoustic wave at the first monitoring microphone 150 is a superposition of the acoustic wave 107 and the acoustic wave 111. In other words, the total signal received by the first monitoring microphone 150 (referred to herein as the first monitoring signal m1(t)) may be represented as a superposition of a first component c(t) from the acoustic wave 107 and a second component n(t) from the acoustic wave 111. This may be represented mathematically as $m1(t)=c(t)+n(t)$.

Due to the spatial separation of the first monitoring microphone 150 and the second monitoring microphone 152, the acoustic wave 107 at the first monitoring position can have an amplitude difference and a delay relative to the acoustic wave 107 at the second monitoring position. Similarly, the acoustic wave 111 at the first monitoring position can have an amplitude difference and a delay relative to the acoustic wave 111 at the second monitoring position. Therefore, the total signal received by the second monitoring microphone 152 (referred to herein as the second monitoring signal m2(t)) may be represented by a superposition of the first component c(t) scaled by a first coefficient $\alpha$ and delayed by a first time delay $\tau_1$, and the second component n(t) scaled by a second coefficient $\delta$ and delayed by a second time delay $\tau 2$. This can be represented mathematically as $m2(t)=\alpha c(t+\tau_1)+\sigma n(t+\tau_2)$.

As described in more detail below, these differences in the first and second monitoring signals m1(t) and m2(t) are used to form a difference signal d(t) which indicates an acoustic energy level due to the acoustic wave 111 within the first earpiece 112. Specifically, the difference signal d(t) is formed such that contributions to the difference signal d(t) due to the acoustic wave 107 are selectively attenuated or entirely removed. The difference signal d(t) is thus formed by processing the first and second monitoring signals m1(t) and m2(t). This processing places a spatial null at the precise location of the transducer 116 generating the acoustic wave 107, while leaving other signals (possibly coming from the same direction) essentially unmodified.

In the illustrated embodiments, the first and second monitoring microphones 150, 152 are arranged along a line extending from the transducer 116. In some embodiments, the first and second monitoring microphones 150, 152 are arranged in an end-fire configuration relative to the centerline of the transducer 116. In some embodiments, more than two monitoring microphones may be used to perform active noise cancellation as described herein.

In various embodiments, where the first and second monitoring microphones 150, 152 are omni-directional microphones that are closely-spaced (e.g., 1-2 cm apart), a beamforming technique may be used to simulate a pair of forwards-facing and backwards-facing directional microphones. The level difference between the outputs of this pair of microphones may be used to determine the acoustic energy within the first earpiece 112 due to the noise 110, which is used to perform active noise cancellation.

As described below, the difference signal d(t) can then be used to adjust the parameters of the transfer function. By adjusting transfer function based on the difference signal d(t), the feedforward signal f(t) can be adjusted so as to achieve optimum noise cancellation at the first listening position 130.

By forming the feedforward signal f(t) based on the decoupled background noise within the first earpiece 112 as indicated by the difference signal d(t), the techniques described herein can accurately model the transfer function from the reference position to the first listening position 130. In doing so, the feedforward active noise cancellation techniques described herein can achieve optimal noise cancellation at the desired location, thereby increasing the quality and robustness of active noise cancellation in diverse acoustic environments.

Figure 3:
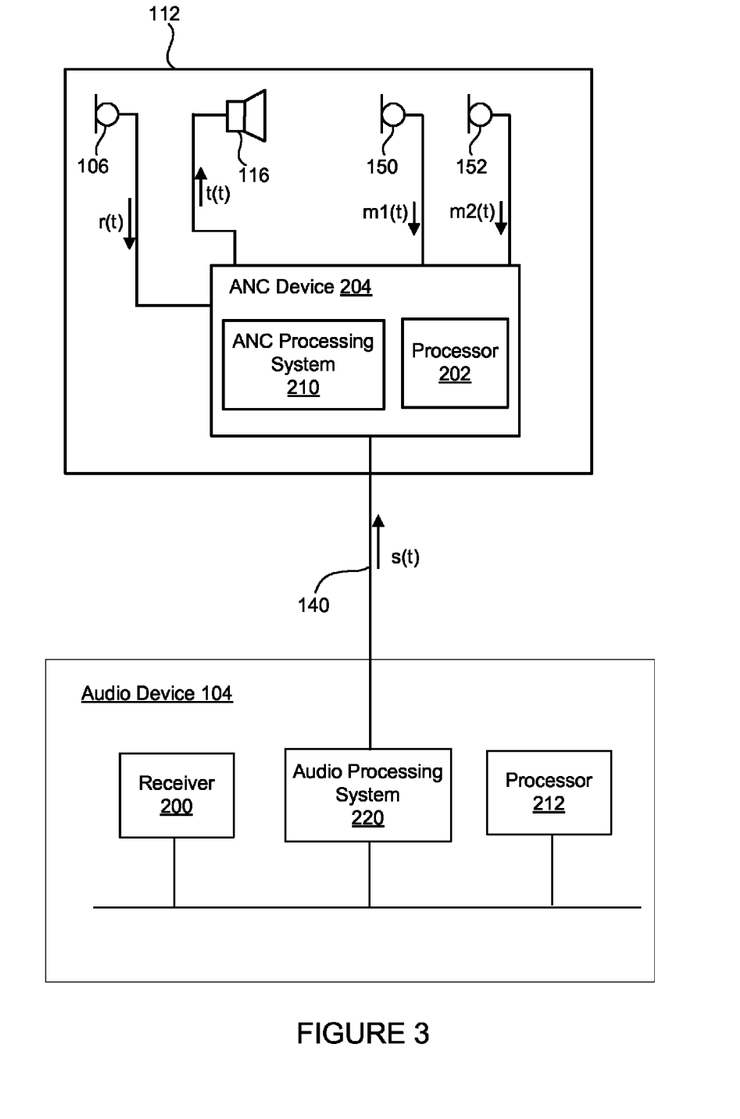
FIG. 3 is a block diagram of an exemplary audio device coupled to an exemplary first earpiece of the headset.

FIG. 3 is a block diagram of an exemplary audio device 104 coupled to an exemplary first earpiece 112 of the headset 120. In the illustrated embodiment the audio device 104 is coupled to the first earpiece 112 via wire 140. The audio device 104 may be coupled to the second earpiece 114 in a similar manner. Alternatively, other mechanisms may be used to couple the audio device 104 to the headset 120.

In the illustrated embodiment, the audio device 104 includes a receiver 200 a processor 212 and an audio processing system 220. The audio device 104 may further include additional or other components necessary for operation of the audio device 104. Similarly, the audio device 104 may include fewer components that perform similar or equivalent functions to those depicted in FIG. 2. In some embodiments, the audio device 104 includes one or more microphones and/or one or more output devices.

Processor 212 may execute instructions and modules stored in a memory (not illustrated in FIG. 3) in the audio device 104 to perform various operations. Processor 212 may include hardware and software implemented as a processing unit, which may process floating operations and other operations for the processor 212.

The exemplary receiver 200 is an acoustic sensor configured to receive a signal from a communications network. In some embodiments, the receiver 200 may comprise an antenna device. The signal may then be forwarded to the audio processing system 220 and provided as audio content to the user 102 via the headset 120 in conjunction with active noise cancellation as described herein. The present technology may be used in one or both of the transmit and receive paths of the audio device 104.

The audio processing system 220 is configured to provide desired audio content to the first earpiece 112 in the form of desired audio signal s(t). Similarly, the audio processing system 220 is configured to provide desired audio content to the second earpiece 114 in the form of a second desired audio signal (not illustrated). The audio content may be retrieved for example from data stored on a storage media such as a memory device, an integrated circuit, a CD, a DVD, etc, for playback to the user 102. The audio content may include a far-end acoustic signal received over a communications network, such as speech of a remote person talking into a second audio device. The desired audio signals may be provided as mono or stereo signals.

An example of the audio processing system 220 in some embodiments is disclosed in U.S. patent application Ser. No. 12/832,920 filed on Jul. 8, 2010 and entitled "Multi-Microphone Robust Noise Suppression", which is incorporated herein by reference.

The exemplary first earpiece 112 includes the reference microphone 106, transducer 116, first monitoring microphone 150, second monitoring microphone 152, and active noise cancellation (ANC) device 204. In some embodiments, more than two monitoring microphones may be used.

The ANC device 204 includes processor 202 and ANC processing system 210. The processor 202 may execute instructions and modules stored in a memory (not illustrated in FIG. 3) in the ANC device 204 to perform various operations, including active noise cancellation as described herein.

The ANC processing system 210 is configured to receive the reference signal r(t) from the reference microphone 106, the first monitoring signal m1(t) from the first monitoring microphone 150, and the second monitoring signal m2(t) from the second monitoring microphone 152, and process the signals. Processing includes performing active noise cancellation as described herein. The ANC processing system 210 is discussed in more detail below.

The acoustic signals received by the reference microphone 106 and the first and second monitoring microphones 150, 152 may be converted into electrical signals. The electrical signals may themselves be converted by an analog to digital converter (not shown) into digital signals for processing in accordance with some embodiments.

In the illustrated embodiment, the active noise cancellation techniques are carried out by the ANC processing system 210 of the ANC device 204. Thus, in the illustrated embodiment the ANC processing system 210 includes resources to form the feedforward signal f(t) used to perform active noise cancellation. Alternatively, the feedforward signal f(t) may be formed utilizing resources within the audio processing system 220 of the audio device 104.

Figure 4:
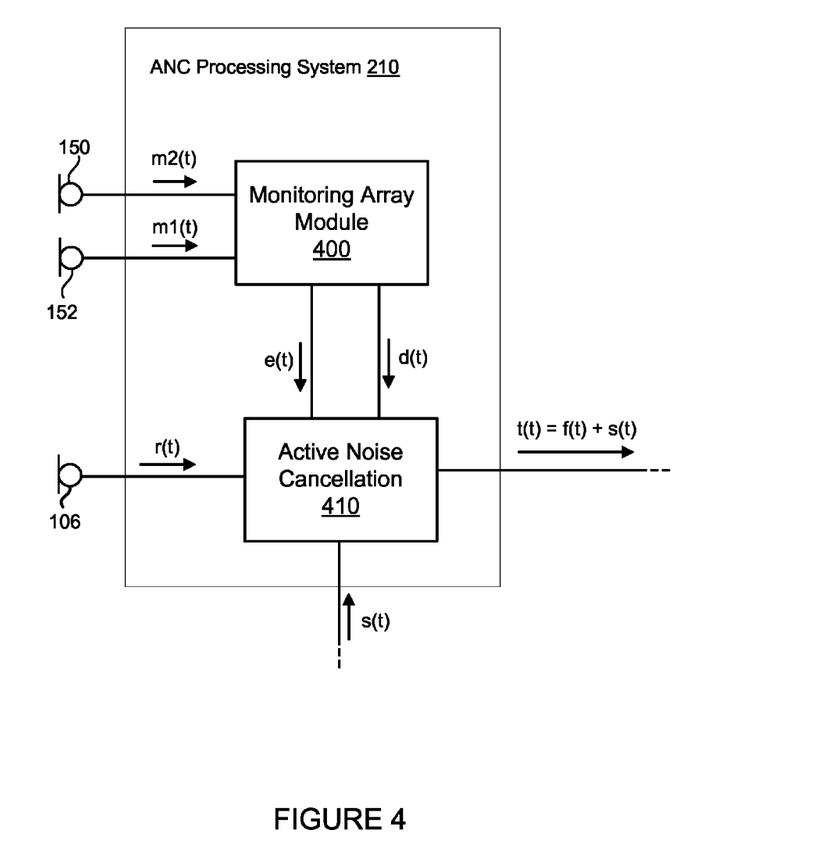
FIG. 4 is a block diagram of en exemplary active noise cancellation (ANC) processing system for performing active noise cancellation as described herein.

FIG. 4 is a block diagram of en exemplary ANC processing system 210 for performing active noise cancellation as described herein. In exemplary embodiments, the ANC processing system 210 is embodied within a memory device within ANC device 204.

The ANC processing system 210 may include monitoring array module 400 and active noise cancellation module 410. The monitoring array module 400 is also referred to herein as a feedback module. The ANC processing system 210 may include more or fewer components than those illustrated in FIG. 4, and the functionality of modules may be combined or expanded into fewer or additional modules. Exemplary lines of communication are illustrated between various modules of FIG. 4, and in other figures herein. The lines of communication are not intended to limit which modules are communicatively coupled with others, nor are they intended to limit the number and type of signals communicated between modules.

In operation, the reference signal r(t) received from the reference microphone 106, the first monitoring signal m1(t) received from the first monitoring microphone 150, and the second monitoring signal m2(t) received from the second monitoring microphone 152 are converted to electrical signals.

The active noise cancellation module 410 receives the reference signal r(t). The active noise cancellation module 410 computes a transfer function which models the acoustic path from the location of the reference microphone 106 to the first listening position 130. The transfer function may incorporate characteristics of the acoustic path, such as one or more of an amplitude, phase shift and time delay from the reference microphone 106 to the first listening position 130. The transfer function can also model the reference microphone 106 response, the transducer 116 response, and the acoustic path from the transducer 116 to the first listening position 130.

The transfer function is then applied to the reference signal r(t) to form the feedforward signal f(t) adapted to cancel the acoustic wave 111 at the first listening position 130.

The parameter values of the transfer function may for example be determined empirically through calibration. The parameter values may for example be stored in the form of a look-up table in the memory within the ANC device 204. As another example, the parameter values may be stored in the form of an approximate function derived based on the calibration measurements.

An acoustic signal t(t), which includes the feedforward signal f(t) and a desired signal s(t) from the audio device 104, is then provided to the audio transducer 116. Active noise cancellation is then performed at the first listening position 130, whereby the audio transducer 116 generates the acoustic wave 107 in response to the acoustic signal t(t). The active noise cancellation module 410 is discussed in more detail below.

The monitoring array module 400 receives the first monitoring signal m1(t) from the first monitoring microphone 150, and the second monitoring signal m2(t) from the second monitoring microphone 152.

As described above, the first monitoring signal m1(t) may be represented as a superposition of a first component c(t) from the acoustic wave 107 and a second component n(t) from the acoustic wave 111. Due to the spatial separation between the first monitoring microphone 150 and the second monitoring microphone 152, the second monitoring signal m2(t) may be represented by a superposition of the first component c(t) scaled by the first coefficient $\alpha$ and delayed by a first time delay $\tau_1$, and the second component n(t) scaled by a second coefficient $\delta$ and delayed by a second time delay $\tau_2$. This can be represented mathematically as $m2(t)=\alpha c(t+\tau_1)+\sigma n(t+\tau_2)$.

The monitoring array module 400 utilizes these differences in the first and second monitoring signals m1(t) and m2(t) to form the difference signal d(t) indicating an acoustic energy level due to the acoustic wave 111 within the first earpiece 112. Specifically, the monitoring array module 400 processes the first and second monitoring signals m1(t) and m2(t) such that contributions to the difference signal d(t) due to the acoustic wave 107 are selectively attenuated or completely removed.

In the illustrated embodiment the difference signal d(t) is formed by weighting and delaying the first monitoring signal m1(t) by the coefficient $\alpha$ and first time delay $\tau_1$, and then subtracting the second monitoring signal m2(t) from the result. This can be expressed as:

$$d(t)=\alpha m1(t+\tau_1)-m2(t)=\alpha[c(t+\tau_1)+n(t+\tau_1)]-[\alpha c(t+\tau_1)+\sigma n(t+\tau_2)]=\alpha n(t+\tau_1)-\sigma n(t+\tau_2)$$

The difference signal d(t) is thus formed by processing which places a spatial null at the precise location of the transducer 116 generating the acoustic wave 107, while leaving other signals due to noise 110 (possibly coming from the same direction as the transducer 116) essentially unmodified.

The difference signal d(t) is then provided to the active noise cancellation module 410. The active noise cancellation module 410 then adjusts the parameters (e.g. filter gain and cutoff frequency) of the transfer function applied to the reference signal r(t) based on the difference signal d(t). As a result, the adjustment modifies the feedforward signal f(t) to optimize noise cancellation at the first listening position 130.

The adjustment of the parameter values of the transfer function based on the difference signal d(t) may for example be determined empirically through calibration. The adjustment values may for example be stored in the form of a look-up table in the memory within the ANC device 204. As another example, the adjustment values may be stored in the form of an approximate function derived based on the calibration measurements.

The feedforward transfer function can be adjusted for example in the following manner. During a calibration stage during which no signal is sent to the transducer 116, the transfer function (Td) is measured between the reference microphone 106 and the difference signal d(t), as well as the transfer function (Te) between the reference microphone 106 and the error signal e(t) for various noise sources, and various positions of the earpiece 112 on the user 102. This provides a mapping between the two transfer functions. Then during normal use, the system can use the difference signal and the reference signal to continuously estimate the transfer function Td. Then the pre-calibrated mapping is use to determine the corresponding transfer function Te, which is then used to compute the feedforward path.

As shown in FIG. 4, the monitoring array module 400 also forms an error signal e(t) which is provided to the active noise cancellation module 410. The error signal e(t) indicates the residual noise that remains within the earpiece 112 after cancellation has taken place (i.e. the superposition of the acoustic wave 111 due to the noise 110 and the acoustic wave 107 generated by the transducer 116). In the illustrated embodiment, the error signal e(t) is one of the first and second monitoring signals m1(t), m2(t).

The error signal e(t) can then also be used by the active noise cancellation module 410 to further adjust the parameter values of the transfer function. In embodiments, the adjustment based on the error signal e(t) occurs when the desired signal s(t) from the audio device 104 is soundless, so that the error signal e(t) is not corrupted by the desired signal s(t) when output by the transducer 116. In such a case, the parameter values of the transfer function may be adjusted to drive the error signal e(t) to zero.

The adjustment of the parameter values of the transfer function based on the error signal e(t) may for example be determined empirically through calibration. The adjustment values may for example be stored in the form of a look-up table in the memory within the ANC device 204. As another example, the adjustment values may be stored in the form of an approximate function derived based on the calibration measurements. The adjustment of the transfer function can be done, in that case using a standard adaptive algorithm such as the filtered-X LMS algorithm (see for example, "Active Noise Control, a tutorial review" by S. M. Kuo and D. R. Morgan, Proceeding of the IEEE, Vol. 87, issue 6, June 1999).

Figure 5:
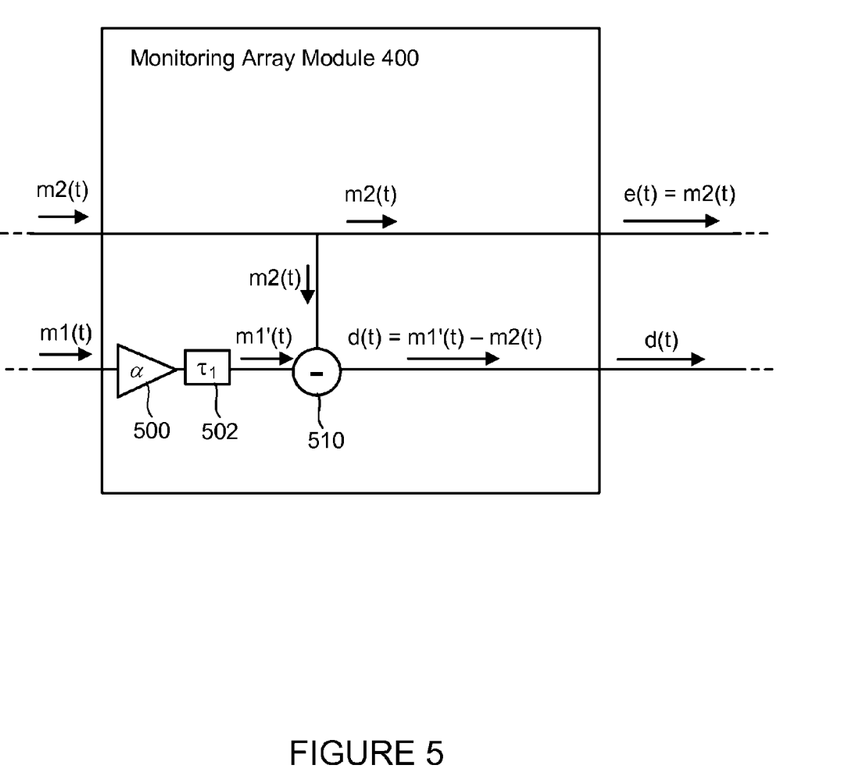
FIG. 5 is a block diagram of an exemplary monitoring array module.

FIG. 5 is a block diagram of an exemplary monitoring array module 400. The monitoring array module 400 may include weighting module 500, delay module 502, and difference module 510. The monitoring array module 400 may include more or fewer components than those illustrated in FIG. 5, and the functionality of modules may be combined or expanded into fewer or additional modules.

The weighting module 500 applies the coefficient $\alpha$ to the first monitoring signal m1(t), and the delay module 502 delays the result by the first time delay $\tau_1$ to form weighted first monitoring signal m1'(t). As described above, the coefficient $\alpha$ and time delay $\tau_1$ are based on the difference between the acoustic wave 107 received by the first and second monitoring microphones 150, 152. The coefficient $\alpha$ and time delay $\tau_1$ may for example be determined empirically through calibration.

In the illustrated embodiment the first monitoring microphone 150 is closer to the transducer 116 than the second monitoring microphone 152. As a result, the energy within the first monitoring signal m1(t) due to the acoustic wave 107 is higher than that within the second monitoring signal m2(t).

In the illustrated embodiment, the coefficient $\alpha$ is applied to the first monitoring signal m1(t). As a result, the coefficient $\alpha$ attenuates the first monitoring signal m1(t), so that the magnitude of the portion of the second monitoring signal m2(t) due to the acoustic wave 107 is the same as the magnitude of the portion of the weighted first monitoring signal m1'(t) due to the acoustic wave 107.

Similarly, the time delay between the acoustic wave 107 incident on the first and second monitoring microphones 150, 152 is dependent upon the distance between the first and second monitoring microphones 150, 152, and the angle of incidence of the acoustic wave 107 upon the first and second monitoring microphones 150, 152. As a result, the time delay $\tau_1$ shifts the first monitoring signal m1(t), so that the portion of the second monitoring signal m2(t) due to the acoustic wave 107 at a given time t is the same as the portion of the weighted first monitoring signal m1'(t) due to the acoustic wave 107.

Other weighting techniques, such as weighting the second monitoring signal m2(t) instead of or in addition to weighting the first monitoring signal m1(t) may alternatively be performed.

The difference module 510 then subtracts the second monitoring signal m2(t) from the weighted first monitoring signal m1'(t) to form the difference signal d(t). The difference signal d(t) can then be provided to the active noise cancellation module 410 to adjust the parameters of the transfer function applied to the reference signal r(t).

In the illustrated embodiment, the error signal e(t) provided by the monitoring array module 400 is the second monitoring signal m2(t). Alternatively, the error signal e(t) may for example be the first monitoring signal m1(t), or as another example be based on both the first and second monitoring signals m1(t), m2(t). The error signal e(t) can then be provided to the active noise cancellation module 410 to further adjust the parameters of the transfer function applied to the reference signal r(t).

In the illustrated embodiment, the error signal e(t) and the difference signal d(t) are formed by processing first and second monitoring signals m1(t), m2(t) in the time domain. Alternatively, the first and second monitoring signals m1(t), m2(t) may be processed in a transform domain. For example, the monitoring array module 400 may include a frequency analysis module which transforms the first and second monitoring signals m1(t) and m2(t) to form sub-band signals m1(k) and m2(k) respectively. In one embodiment, the frequency analysis module takes the signals and mimics the frequency analysis of the cochlea (e.g., cochlear domain), simulated by a filter bank, for each time frame. The frequency analysis module separates each of the first monitoring signal m1(t) and the second monitoring signal m2(t) into two or more frequency sub-band signals. A sub-band signal is the result of a filtering operation on an input signal, where the bandwidth of the filter is narrower than the bandwidth of the signal received by the frequency analysis module. Alternatively, other filters such as short-time Fourier transform (STFT), sub-band filter banks, modulated complex lapped transforms, cochlear models, wavelets, etc., can be used for the analysis and synthesis.

Because most sounds (e.g. acoustic signals) are complex and include more than one frequency, a sub-band analysis on the acoustic signal determines what individual frequencies are present in each sub-band of the complex acoustic signal during a frame (e.g. a predetermined period of time). For example, the length of a frame may be 4 ms, 8 ms, or some other length of time. In some embodiments there may be no frame at all. The results may include sub-band signals in a fast cochlea transform (FCT) domain. The sub-band signals of the first monitoring signal m1(t) are expressed as m1(k), and the sub-band signals of the second monitoring signal m2(t) are expressed as m2(k). The sub-band signals m1(k) and m2(k) may then be used to form sub-band difference signals d(k) and sub-band error signals e(k) used to adjust the parameter values of the transfer function.

Due to the spatial separation between the first monitoring microphone 150 and the second monitoring microphone 152, the difference between the sub-band signals m1(k) and the sub-band signals m2(k) may be represented by complex coefficients. Similar to the techniques described above, the monitoring array module 400 utilizes these differences in the sub-band signals m1(k) and m2(k) to form the sub-band difference signals d(k) indicating an acoustic energy level due to the acoustic wave 111 within the first earpiece 112. Specifically, the monitoring array module 400 processes the sub-band signals m1(k) and m2(k) such that contributions to the sub-band difference signals d(k) due to the acoustic wave 107 are selectively attenuated or completely removed.

Figure 6:
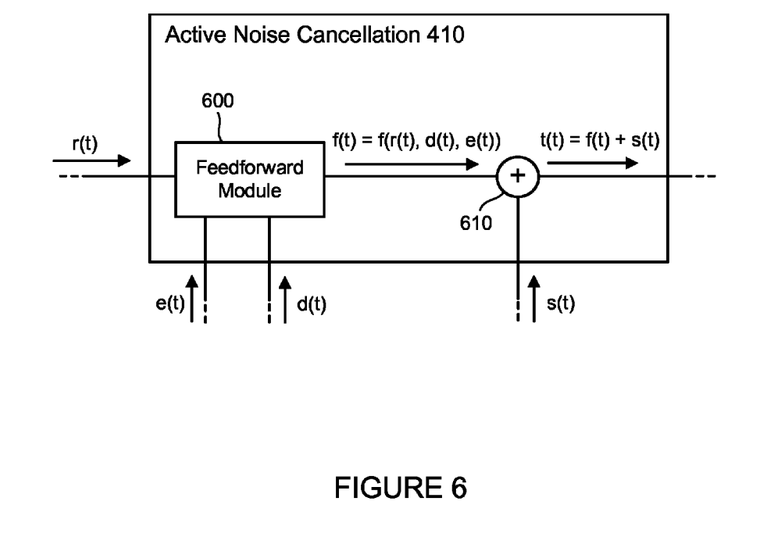
FIG. 6 is a block diagram of an exemplary active noise cancellation module.

FIG. 6 is a block diagram of an exemplary active noise cancellation module 410. The active noise cancellation module 410 may include feedforward module 600 and summing module 610. The active noise cancellation module 410 may include more or fewer components than those illustrated in FIG. 6, and the functionality of modules may be combined or expanded into fewer or additional modules.

The feedforward module 600 receives the reference signal r(t), the error signal e(t), and the difference signal d(t). The feedforward module 600 applies the transfer function to the reference signal r(t) to form the feedforward signal f(t) adapted to cancel the acoustic wave 111 at the first listening position 130 using the techniques described herein. The feedforward module 600 also adjusts the transfer function based on the error signal e(t) and the difference signal d(t) as described above.

The summing module 610 adds the feedforward signal f(t) to the desired audio signal s(t) from the audio device 104 to form the acoustic signal t(t). The acoustic signal t(t) can then be provided to the first earpiece 112 of the headset 120 to perform active noise cancellation at the first listening position 130 as described herein.

The techniques described herein can also be implemented to form a second acoustic signal which can be provided to the second earpiece 114 of the headset 120 to perform active noise cancellation at the second listening position 132.

In the illustrated embodiment the acoustic signal t(t) is formed by addition in the time-domain. In some embodiments in which the feedforward signal and the desired audio signal are processed in the transform domain, the addition may take place in the transform domain, and the results then transformed into the time domain to form the acoustic signal t(t).

In the illustrated embodiment, the feedforward signal f(t) is formed by processing the reference signal r(t) in the time domain. Alternatively, the reference signal r(t) may be transformed into a transform domain given by sub-band signals r(k). The sub-band signals r(k) may then be processed in the transform domain to form sub-band feedforward signals f(k), and the result then transformed into the time domain to form the feedforward signal f(t).

Figure 7:
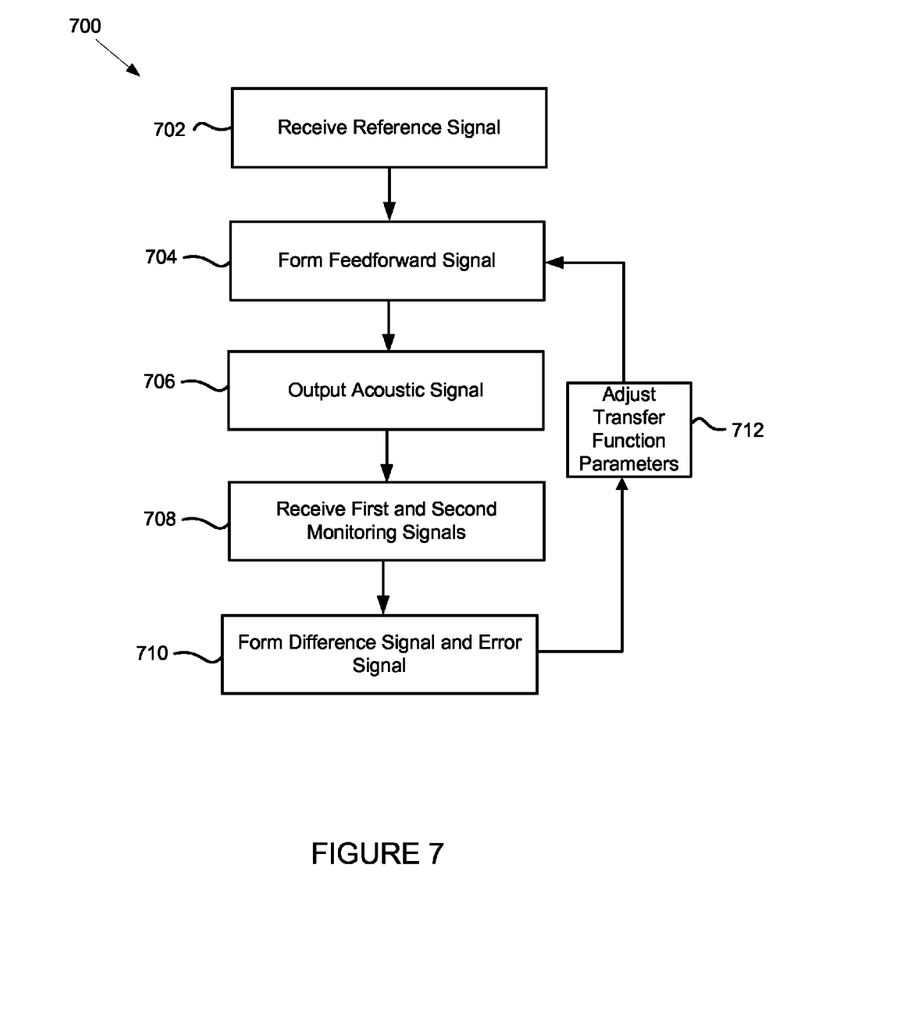
FIG. 7 is a flow chart of an exemplary method for performing active noise cancellation.

FIG. 7 is a flow chart of an exemplary method 700 for performing active noise cancellation. As with all flow charts herein, in some embodiments the steps may be combined, performed in parallel, or performed in a different order. The method 700 of FIG. 7 may also include addition or fewer steps than those illustrated.

In step 702, the reference signal r(t) is received by the reference microphone 106. In exemplary embodiments, the reference signal r(t) is converted to digital format for processing. In some embodiments, more than one reference signal may be received and processed.

In step 704, the feedforward signal f(t) is formed by applying the transfer function to the reference signal r(t). As described above, the transfer function models the acoustic path from the location of the reference microphone 106 to the first listening position 130.

In step 706, the feedforward signal f(t) is combined with the desired audio signal s(t) to form the acoustic signal t(t). The acoustic signal t(t) can then be provided to the transducer 116 of the first earpiece 112 of the headset 120 to generate the acoustic wave 107, thereby perform active noise cancellation at the first listening position 130.

In step 708, the first monitoring signal m1(*t*) is received by the first monitoring microphone 150, and the second monitoring signal m2(*t*) is received by the second monitoring microphone 152.

In step 710, the difference signal d(t) and the error signal e(t) are formed based on the first and second monitoring signals m1(*t*), m2(*t*) using the techniques described herein.

In step 712, the parameters (e.g. filter gain and cutoff frequency) of the transfer function applied to the reference signal r(t) are adjusted based on the difference signal d(t) and optionally the error signal e(t). As a result, the adjustment modifies the feedforward signal f(t) formed at step 704 to optimize active noise cancellation at the first listening position 130.

As shown in FIG. 7, step 712 is a feedback loop which can continuously adapt the parameters of the transfer function applied to the reference signal r(t) based on the changes over time in the difference signal d(t). By doing so, the feedforward active noise cancellation techniques described herein can achieve optimal noise cancellation in diverse and dynamic acoustic environments.

As described above with respect to FIG. 2, the acoustic wave 111 due to the noise 110 is picked up by the reference microphone 106. In addition, part of the acoustic wave 107 output by the transducer 116 may be reflected back and picked up by the reference microphone 106. In such a case, the acoustic wave 107 output by the transducer 116 may corrupt the reference signal r(t). As described below with respect to FIG. 8, reference signal r(t) may be formed such that contributions due to the acoustic wave 107 are selectively attenuated or entirely removed.

Figure 8:
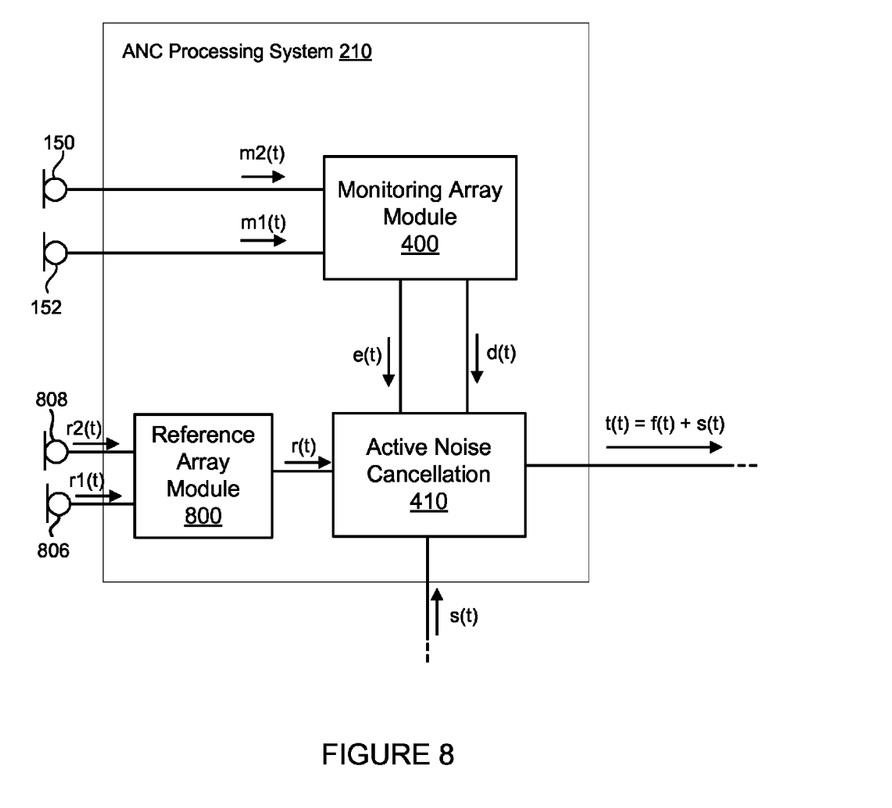
FIG. 8 illustrates a second block diagram of an exemplary ANC processing system coupled to a first reference microphone and a second reference microphone

FIG. 8 illustrates a second block diagram of an exemplary ANC processing system 210 coupled to a first reference microphone 806 and to a second reference microphone 808.

Similar to the discussion above with respect to the formation of the difference signal d(t), the ANC processing system 210 processes reference signals r1(*t*), r2(*t*) received by the first and second reference microphones 806, 808 to form the reference signal r(t). Specifically, the reference signal r(t) is formed such that contributions to the reference signal r(t) due to the acoustic wave 107 are selectively attenuated or entirely removed.

In the illustrated embodiments, the first and second reference microphones 806, 808 are arranged on the outside the first earpiece 112 (e.g. proximate the location of the reference microphone 106 illustrated FIG. 2) at first and second reference positions respectively. The first and second reference microphones 806, 808 may be arranged along a line extending from the transducer 116. In some embodiments, the first and second reference microphones 806, 808 are arranged in an end-fire configuration relative to the centerline of the transducer 116. In some embodiments, more than two reference microphones may be used.

In FIG. 8, the ANC processing system 210 includes a reference array module 800. The reference array module 800 receives the first reference signal r1(*t*) from the first reference microphone 806, and the second reference signal r2(*t*) from the second reference microphone 808.

The first reference signal r1(*t*) may be represented as a superposition of a first component x(t) from the acoustic wave 107 and a second component y(t) from the acoustic wave 111. Due to the spatial separation between the first reference microphone 806 and the second reference microphone 808, the differences between the first reference signal r1(*t*) and the second reference microphone r2(*t*) can be represented by coefficients and time delays. Thus, the second reference signal r2(*t*) may be represented by a superposition of the first component x(t) scaled by a first coefficient δ and delayed by a time delay $\tau_3$, and the second component y(t) scaled by a second coefficient E and delayed by a time delay $\tau_4$. This can be represented mathematically as r2(*t*)=δx(t+$t_3$)+εy(t+$\tau_4$).

The reference array module 800 utilizes these differences to form the reference signal r(t) indicating an acoustic energy level due to the acoustic wave 111 outside the first earpiece 112. Specifically, the reference array module 800 processes the first and second reference signals r1(*t*) and r2(*t*) such that contributions to the reference signal r(t) due to the acoustic wave 107 are selectively attenuated.

In the illustrated embodiment the reference signal r(t) is formed by weighting and delaying the first reference signal r1(*t*) by the coefficient δ and time delay $\tau_3$, and then subtracting the second reference signal r2(*t*) from the result. This can be expressed as:

$$r(t)=\delta r1(t+\tau_3)-r2(t)=\delta[x(t+\tau_3)+y(t+\tau_3)]-[\delta x(t+\tau_3)+\epsilon y(t+\tau_4)]=\delta y(t+\tau_3)-\epsilon y(t+\tau_4)$$

The reference signal r(t) is thus formed by processing which places a spatial null at the precise location of the transducer 116 generating the acoustic wave 107, while leaving other signals due to noise 110 (possibly coming from the same direction as the transducer 116) essentially unmodified. The reference signal r(t) is then provided to the active noise cancellation module 410 to perform active noise cancellation as described herein.

Figure 9:
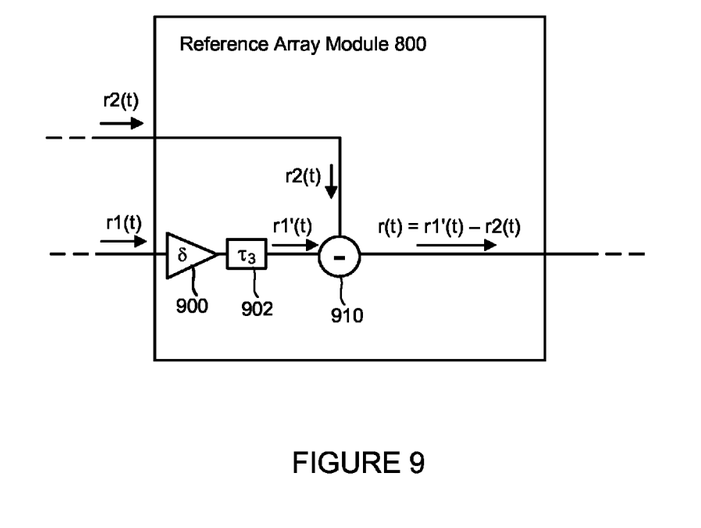
FIG. 9 is a block diagram of an exemplary reference array module.

FIG. 9 is a block diagram of an exemplary reference array module 800. The reference array module 800 may include weighting module 900, delay module 902 and difference module 910. The reference array module 800 may include more or fewer components than those illustrated in FIG. 9, and the functionality of modules may be combined or expanded into fewer or additional modules.

The weighting module 900 applies the coefficient δ to the first reference signal r1(*t*). The delay module 902 then applies a time delay $\tau_3$ to the result to form weighted reference monitoring signal r1'(t). As described above, the coefficient δ and time delay $\tau_3$ are based on the difference between the acoustic wave 107 received by the first and second reference microphones 806, 808. The coefficient δ and time delay $\tau_3$ may for example be determined through calibration.

In the illustrated embodiment the first reference microphone 806 is closer to the transducer 116 than the second reference microphone 808. As a result, the energy within the first reference signal r1(*t*) due to the acoustic wave 107 is higher than that within the second reference signal r2(*t*).

In the illustrated embodiment, the coefficient δ is applied to the first reference signal r1(*t*). As a result, the coefficient δ attenuates the first reference signal r1(*t*), so that the magnitude of the portion of the second reference signal r2(*t*) due to the acoustic wave 107 is the same as the magnitude of the portion of the weighted first reference signal r1'(t) due to the acoustic wave 107.

Similarly, the time delay of the acoustic wave 107 incident on the first and second reference microphones 806, 808 is dependent upon the distance between the first and second reference microphones 806, 808, and the angle of incidence of the acoustic wave 107 upon the first and second reference microphones 806, 808. As a result, applying the time delay $\tau_3$ shifts the first reference signal r1(*t*), so that the portion of the second reference signal r2(*t*) due to the acoustic wave 107 at a given time t is the same as the portion of the weighted first reference signal r1'(t) due to the acoustic wave 107.

Other weighting techniques, such as weighting the second reference signal r2(*t*) instead of or in addition to weighting the first reference signal r1(*t*) may alternatively be performed.

The difference module 910 then subtracts the second reference signal r2(t) from the weighted first reference signal r1'(t) to form the reference signal r(t). The reference signal r(t) can then be provided to the active noise cancellation module 410 to perform active noise cancellation as described herein. In some alternative embodiments, the reference signal r(t) may be formed through processing of the first and second reference signals r1(t), r2(t) in the transform domain. In such a case, the transform domain representation of the reference signal r(t) given by sub-band signals r(k) may be provided to the active noise cancellation module 410 to perform active noise cancellation.

The above described modules may be comprised of instructions that are stored in a storage media such as a machine readable medium (e.g., computer readable medium). These instructions may be retrieved and executed by a processor. Some examples of instructions include software, program code, and firmware. Some examples of storage media comprise memory devices and integrated circuits. The instructions are operational.

While the present invention is disclosed by reference to the preferred embodiments and examples detailed above, it is to be understood that these examples are intended in an illustrative rather than a limiting sense. It is contemplated that modifications and combinations will readily occur to those skilled in the art, which modifications and combinations will be within the spirit of the invention and the scope of the following claims.

What is claimed is:

1. A method for reducing an acoustic energy level at a listening position, the method comprising:
    generating a feedforward signal from a primary acoustic wave received at a reference position;
    generating a secondary acoustic wave based on the feedforward signal, the secondary acoustic wave adapted to reduce the acoustic energy level at the listening position;
    receiving the primary and secondary acoustic waves at a first monitoring position to form a first monitoring signal, and receiving the primary and secondary acoustic waves at a second monitoring position to form a second monitoring signal;
    forming a feedback signal based on the first and second monitoring signals, the feedback signal indicating an acoustic energy level of the primary acoustic wave at the listening position; and
    modifying the feedforward signal based on the feedback signal.

2. The method of claim 1, wherein the first and the second monitoring positions are arranged between the listening position and a source of the secondary acoustic wave, and forming the feedback signal comprises performing a difference operation on the first and second monitoring signals, the difference operation adapted to place a spatial null at the source to cancel secondary acoustic wave contributions to the feedback signal due to the first and second monitoring signals.

3. The method of claim 2, wherein the difference operation is based on a spatial distance between the first and second monitoring positions.

4. The method of claim 1, wherein the first and the second monitoring positions are arranged along a line extending from the source.

5. The method of claim 1, further comprising forming a second feedback signal based on at least one of the first and second monitoring signals, the second feedback signal indicating a total acoustic energy level at the listening position due to the primary and the secondary acoustic waves, and wherein modifying the feedforward signal is further based on the second feedback signal.

6. The method of claim 5, wherein the second feedback signal is based on one of the first and second monitoring signals.

7. The method of claim 1, wherein generating the feedforward signal comprises:
    receiving the primary and secondary acoustic waves at a first reference position to form a first reference signal, and receiving the primary and second acoustic waves at a second reference position to form a second reference signal;
    combining the first and second reference signals to form a reference signal, the combining adapted to suppress secondary acoustic wave contributions to the reference signal due to the first and second reference signals; and
    applying a transfer function to the reference signal to form the feedforward signal.

8. The method of claim 7, wherein combining the first and second reference signals places a spatial null at a source of the secondary acoustic wave.

9. A system for reducing an acoustic energy level at a listening position, the system comprising:
    a reference microphone to receive a primary acoustic wave at a reference position to form a reference signal;
    a feedforward module to generate a feedforward signal based on the reference signal;
    an audio transducer to generate a secondary acoustic wave based on the feedforward signal, the secondary acoustic wave adapted to reduce the acoustic energy level at the listening position;
    a first monitoring microphone to receive the primary and secondary acoustic waves at a first monitoring position to form a first monitoring signal;
    a second monitoring microphone to receive the primary and secondary acoustic waves at a second monitoring position to form a second monitoring signal; and
    a feedback module to form a feedback signal based on the first and second monitoring signals, the feedback signal indicating an acoustic energy level of the primary acoustic wave at the listening position, and wherein the feedforward module modifies the feedforward signal based on the feedback signal.

10. The system of claim 9, wherein the first and the second monitoring microphones are arranged between the listening position and the audio transducer, and the feedback module performs a difference operation on the first and second monitoring signals to form the feedback signal, the difference operation adapted to place a spatial null at the location of the audio transducer to cancel secondary acoustic wave contributions to the feedback signal due to the first and second monitoring signals.

11. The system of claim 10, wherein the difference operation is based on a spatial distance between the first and second monitoring positions.

12. The system of claim 9, wherein the first and the second monitoring positions are arranged along a line extending from the audio transducer.

13. The system of claim 9, wherein the feedback module further forms a second feedback signal based on at least one of the first and second monitoring signals, the second feedback signal indicating a total acoustic energy level at the listening position due to the primary and second acoustic waves, and wherein the feedforward module modifies the feedforward signal further based on the second feedback signal.

14. The system of claim 13, wherein the second feedback signal is based on one of the first and second monitoring signals.

15. The system of claim 9, further comprising a first reference microphone to receive the primary and secondary acoustic waves at a first reference position to form a first reference signal, a second reference microphone to receive the primary and secondary acoustic waves at a second reference position to form a second reference signal, and wherein the feedforward module combines the first and second reference signals to form the reference signal such that secondary acoustic wave contributions to the reference signal due to the first and second reference signals are suppressed, and applies a transfer function to the reference signal to form the feedforward signal.

16. The system of claim 15, wherein combining the first and second reference signals places a spatial null at the location of the audio transducer.

17. A non-transitory computer readable storage medium having embodied thereon a program, the program being executable by a processor to perform a method for reducing an acoustic energy level at a listening position, the method comprising:
  generating a feedforward signal from a primary acoustic wave received at a reference position;
  generating a secondary acoustic wave based on the feedforward signal, the secondary acoustic wave adapted to reduce the acoustic energy level at the listening position;
  receiving the primary and secondary acoustic waves at a first monitoring position to form a first monitoring signal, and receiving the primary and secondary acoustic waves at a second monitoring position to form a second monitoring signal;
  forming a feedback signal based on the first and second monitoring signals, the feedback signal indicating an acoustic energy level of the primary acoustic wave at the listening position; and
  modifying the feedforward signal based on the feedback signal.

18. The non-transitory computer readable storage medium of claim 17, wherein the first and the second monitoring positions are arranged between the listening position and a source of the secondary acoustic wave, and forming the feedback signal comprises performing a difference operation on the first and second monitoring signals, the difference operation adapted to place a spatial null at the source to cancel secondary acoustic wave contributions to the feedback signal due to the first and second monitoring signals.

19. The non-transitory computer readable storage medium of claim 17, further comprising forming a second feedback signal based on at least one of the first and second monitoring signals, the second feedback signal indicating a total acoustic energy level at the listening position due to the primary and the secondary acoustic waves, and wherein modifying the feedforward signal is further based on the second feedback signal.

20. The non-transitory computer readable storage medium of claim 17, wherein generating the feedforward signal comprises:
  receiving the primary and secondary acoustic waves at a first reference position to form a first reference signal, and receiving the primary and second acoustic waves at a second reference position to form a second reference signal;
  combining the first and second reference signals to form a reference signal, the combining adapted to suppress secondary acoustic wave contributions to the reference signal due to the first and second reference signals; and
  applying a transfer function to the reference signal to form the feedforward signal.

* * * * *